United States Patent
Zhao

(10) Patent No.: US 11,234,359 B2
(45) Date of Patent: Feb. 1, 2022

(54) METHOD AND DEVICE FOR SOIL MOISTURE RETRIEVAL USING MULTI-CHANNEL COLLABORATIVE ALGORITHM AND PASSIVE MICROWAVE RADIOMETRY

(71) Applicant: Aerospace Information Research Institute, Chinese Academy of Sciences, Beijing (CN)

(72) Inventor: Tianjie Zhao, Beijing (CN)

(73) Assignee: Aerospace Information Research Institute, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/011,536

(22) Filed: Sep. 3, 2020

(65) Prior Publication Data
US 2021/0337721 A1    Nov. 4, 2021

(30) Foreign Application Priority Data
Apr. 30, 2020  (CN) .......................... 202010364720.1

(51) Int. Cl.
*A01C 14/00* (2006.01)
*G05B 19/4155* (2006.01)

(52) U.S. Cl.
CPC .......... *A01C 14/00* (2013.01); *G05B 19/4155* (2013.01); *G05B 2219/39266* (2013.01)

(58) Field of Classification Search
CPC ................ A01C 14/00; G05B 19/4155; G05B 2219/39266; G01N 22/04
See application file for complete search history.

(56) References Cited

U.S. PATENT DOCUMENTS

| | | | | |
|---|---|---|---|---|
| 4,310,758 A | * | 1/1982 | Peterson | G01N 33/246 250/255 |
| 8,367,420 B1 | * | 2/2013 | Sridhar | G01N 21/314 436/119 |

(Continued)

FOREIGN PATENT DOCUMENTS

| | | |
|---|---|---|
| CN | 101936921 A | 1/2011 |
| CN | 102628860 A | 8/2012 |

(Continued)

OTHER PUBLICATIONS

Xingming Zheng et al. A New Soil Moisture Retrieval Algorithm from the L-Band Passive Microwave Brightness Temperature Based on the Chane Detection Principle. Remote SEnsing vol. 12. No. 8: 1-14 Apr. 20, 2020.

*Primary Examiner* — Jamie L McGowan
(74) *Attorney, Agent, or Firm* — CBM Patent Consulting, LLC

(57) ABSTRACT

A method for soil moisture retrieval using multi-channel collaboration algorithm and passive microwave radiometry including: establishing mathematical relationship formula between brightness temperatures at any two channels according to microwave radiative transfer equation; collecting actual brightness temperatures of core channel and collaborative channels; selecting parameters to be retrieved including soil moisture value; giving a series of estimated values of parameters to be retrieved, calculating a series of predicted brightness temperatures of collaborative channels according to actual brightness temperature of core channel, microwave radiative transfer equation and mathematical relationship formula, comparing predicted brightness temperatures with actual brightness temperature, and determining soil moisture value.

8 Claims, 6 Drawing Sheets

(56) References Cited

U.S. PATENT DOCUMENTS

| | | | | |
|---|---|---|---|---|
| 8,655,601 B1* | 2/2014 | Sridhar | ................ | G01N 33/24 |
| | | | | 702/23 |
| 9,864,094 B2* | 1/2018 | Stoller | ................ | G01V 8/10 |
| 2017/0343485 A1* | 11/2017 | Garrison | ................ | G01S 17/48 |

FOREIGN PATENT DOCUMENTS

| | | | |
|---|---|---|---|
| CN | 103149220 A | | 6/2013 |
| CN | 105606631 A | | 5/2016 |
| CN | 106018439 A | | 10/2016 |
| CN | 108982548 A | | 12/2018 |
| EP | 0891541 A | | 1/1999 |

* cited by examiner establishing a mathematical relationship formula between brightness temperatures at any two channels according to a microwave radiative transfer equation;

⇓ collecting an actual brightness temperature of a core channel and an actual brightness temperature of collaborative channels;

⇓ selecting parameters to be retrieved, wherein the parameters comprises at least a soil moisture value;

⇓ giving a series of estimated values of parameters to be retrieved, calculating a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value among the series of estimated values of parameters to be retrieved according to a comparison result; or giving initial values of parameters to be retrieved, performing iterative calculation to obtain a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value according to the comparison result.

Fig.1

METHOD AND DEVICE FOR SOIL MOISTURE RETRIEVAL USING MULTI-CHANNEL COLLABORATIVE ALGORITHM AND PASSIVE MICROWAVE RADIOMETRY

TECHNICAL FIELD

The present invention relates to the field of quantitative remote sensing, and more particularly to a method and device for soil moisture retrieval using multi-channel collaboration algorithm and passive microwave radiometry.

BACKGROUND

The remote sensing observation of soil moisture mainly depends on a microwave remote sensing technology. Especially, the soil moisture at a global scale can be obtained by a space-borne passive microwave radiometer within 2 to 3 days. At present, the soil moisture retrieval algorithms are generally developed for specific satellite payload configurations, which can be divided into the following three categories: (1) a reverse solution based on the radiative transfer equation; (2) an iterative solution based on the radiative transfer equation; and (3) an analytical solution with certain indices from microwave observations. The above-mentioned retrieval algorithms comprise the following disadvantages and limitations: methods (1) and (2) require auxiliary data to assist in the retrieval process. For example, prior information on vegetation, such as the vegetation water content from the auxiliary optical images have to be used to account for vegetation effects in the reverse solution of the method (1) to derive the soil moisture. In the iterative retrieval solution of the method (2), the differences between radiative transfer model simulations and satellite observations are minimized through a certain cost function to obtain a solution result of soil moisture. Because a situation of multiple minima (multiple solutions) are prone to occur in this process, the auxiliary data is generally used as an initial value or as upper and lower bounds of unknown parameters to constrain the retrieval results. The method (3) is used for performing an analytical solving of the radiative transfer equation. There are many parameters in the radiative transfer equation that affect observed brightness temperature of the Earth land surfaces. The model has to be simplified to obtain an analytical solution. Generally, it is assumed that the vegetation effects are polarization independent or there is no vegetation scattering effects. In fact, these assumptions and neglections are not in line with the actual situation, so the retrieval results of soil moisture are inconsistent with the ground-based observations. Therefore, a technical solution that can overcome the above deficiencies at least in some ways is urgently needed.

SUMMARY

An object of the present invention is to provide a method and device for soil moisture retrieval using multi-channel collaboration algorithm and passive microwave radiometry. In the retrieval process, it does not rely on the auxiliary data as inputs or constrains for vegetation properties, does not need to neglect the scattering effects and polarization dependences of vegetation, and reduces the situation of multiple solutions and uncertainty during the retrieval process.

In order to achieve these objects and other advantages according to the present invention, the present invention provides a method for soil moisture retrieval using multi-channel collaboration algorithm and passive microwave radiometry, comprising the following steps:

establishing a mathematical relationship formula between brightness temperatures at any two channels according to a microwave radiative transfer equation;

collecting an actual brightness temperature of a core channel and actual brightness temperatures of collaborative channels;

selecting parameters to be retrieved, wherein the parameter comprises at least a soil moisture value;

giving a series of estimated values of the parameters to be retrieved, calculating a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value among the series of estimated values of the parameters to be retrieved according to a comparison result; or giving initial values of parameters to be retrieved, performing iterative calculation to obtain a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value according to the comparison result.

Preferably, in some embodiments of the method for soil moisture retrieval using multi-channel collaboration algorithm and passive microwave radiometry, the microwave radiative transfer equation is represented by a two-component model under the zero-order approximation.

Preferably, in some embodiments of the method for soil moisture retrieval using multi-channel collaboration algorithm and passive microwave radiometry, the mathematical relationship formula is written as:

$$Tb_{ch(2)}^{total} = V_{ch(2)}^{e} - S_r V_r \cdot V_{ch(1)}^{e} + S_r V_r \cdot Tb_{ch(1)}^{total}$$

$$S_r = \frac{e_{ch(2)}^{s}}{e_{ch(1)}^{s}}$$

$$V_r = \frac{V_{ch(2)}^{t}}{V_{ch(1)}^{t}}$$

wherein, $Tb_{ch(2)}^{total}$ and $Tb_{ch(1)}^{total}$ are brightness temperatures at any two channels, $e_{ch(2)}^{s}$ and $e_{ch(2)}^{s}$ are microwave emissivity of the rough soil surface at the any two channels, $V_{ch(2)}^{t}$ and $V_{ch(1)}^{t}$ are vegetation transmission term at the any two channels, and $V_{ch(1)}^{e}$ and $V_{ch(2)}^{e}$ are vegetation emission term at the any two channels.

Preferably, in some embodiments of the method for soil moisture retrieval using multi-channel collaboration algorithm and passive microwave radiometry, at least one of frequency, incidence angle or polarization is different between the any two channels of the core channel and the collaborative channels.

Preferably, in some embodiments of the method for soil moisture retrieval using multi-channel collaboration algorithm and passive microwave radiometry, according to estimated values of one or more parameters to be retrieved, the actual brightness temperature of the core channel, and the microwave radiative transfer equation, estimated values of other one or more parameters to be retrieved are calculated;

the value of the parameters to be retrieved of the collaborative channels is determined according to a relationship between parameters to be retrieved at any two channels; and the predicted brightness temperatures of the collaborative channels are calculated according to the value of parameters to be retrieved of the collaborative channels and the mathematical relationship formula.

Preferably, in some embodiments of the method for soil moisture retrieval using multi-channel collaboration algorithm and passive microwave radiometry, the number of channels comprised in the core channel and the collaborative channels is not less than the number of the parameters to be retrieved.

Preferably, in some embodiments of the method for soil moisture retrieval using multi-channel collaboration algorithm and passive microwave radiometry, the parameter to be retrieved further comprises vegetation optical depth; and a relationship between vegetation optical depths at any two channels is:

$$\frac{\tau^0_{ch(1)}}{\tau^0_{ch(2)}} = \left(\frac{f_1}{f_2}\right)^x$$

wherein, $\tau_{ch(1)}{}^0$ and $\tau_{ch(2)}{}^0$ are vegetation optical depths at frequency $f_1$ and frequency $f_2$, respectively, and x is a parameter depending on a vegetation type.

Preferably, in some embodiments of the method for soil moisture retrieval using multi-channel collaboration algorithm and passive microwave radiometry, the predicted brightness temperatures of the collaborative channels and the actual brightness temperature are compared by establishing a cost function.

Preferably, in some embodiments of the method for soil moisture retrieval using multi-channel collaboration algorithm and passive microwave radiometry, the method comprises establishing the cost function, wherein the cost function is:

$$\min \Phi = \sum_{i=2}^{N} \frac{(Tb^{estimated}_{ch(i)} - Tb^{total}_{ch(i)})^2}{Tb^{total}_{ch(i)}};$$

selecting the minimum value of the cost function and an estimated soil moisture value corresponding to the minimum value of the cost function from comparison between predicted and actual observed brightness temperatures at the collaborative channels; and taking the estimated soil moisture value as the retrieval results of soil moisture value.

The present invention further provides a retrieval device for soil moisture retrieval using multi-channel collaboration algorithm and passive microwave radiometry, comprising:
a processor;
a memory, which stores an executable instruction;
wherein, the processor is configured to execute the executable instruction for performing the method for soil moisture retrieval using multi-channel collaboration algorithm and passive microwave radiometry.

The present invention comprises at least the following beneficial effects:
the retrieval is performed in the present invention to obtain the soil moisture and vegetation optical depth by using mutual collaboration of multi-frequency, multi-angular or multi-polarization observations. In the retrieval process, (1) the core channel brightness temperature observed by passive microwave radiometry is directly used to obtain a set of candidate parameters for the retrieval of soil moisture and vegetation optical depth. This process reduces the multiple solutions when solving the radiative transfer model. (2) Then the observation of the collaborative channels is used, and the cost function is established to filter out the set to be retrieved and determine the retrieval results. This process utilizes all the information from the collaborative channels to guarantee the retrieval results are robust. The retrieval process does not rely on the auxiliary data, especially the vegetation data, and does not need to neglect scattering effects and polarization dependences of vegetation. Multi-channels data are used to determine the parameters to be retrieved by the collaborative equation, which reduces a situation of multiple solutions and retrieval uncertainties.

Other advantages, objects, and features of the present invention will be showed in part through the following description, and will be understood in part by those skilled in the art from study and practice of the present invention.

BRIEF DESCRIPTION OF THE DRAWINGS

FIG. 1 is a flowchart according to the present invention.

DETAILED DESCRIPTION OF EMBODIMENTS

Figure 2:
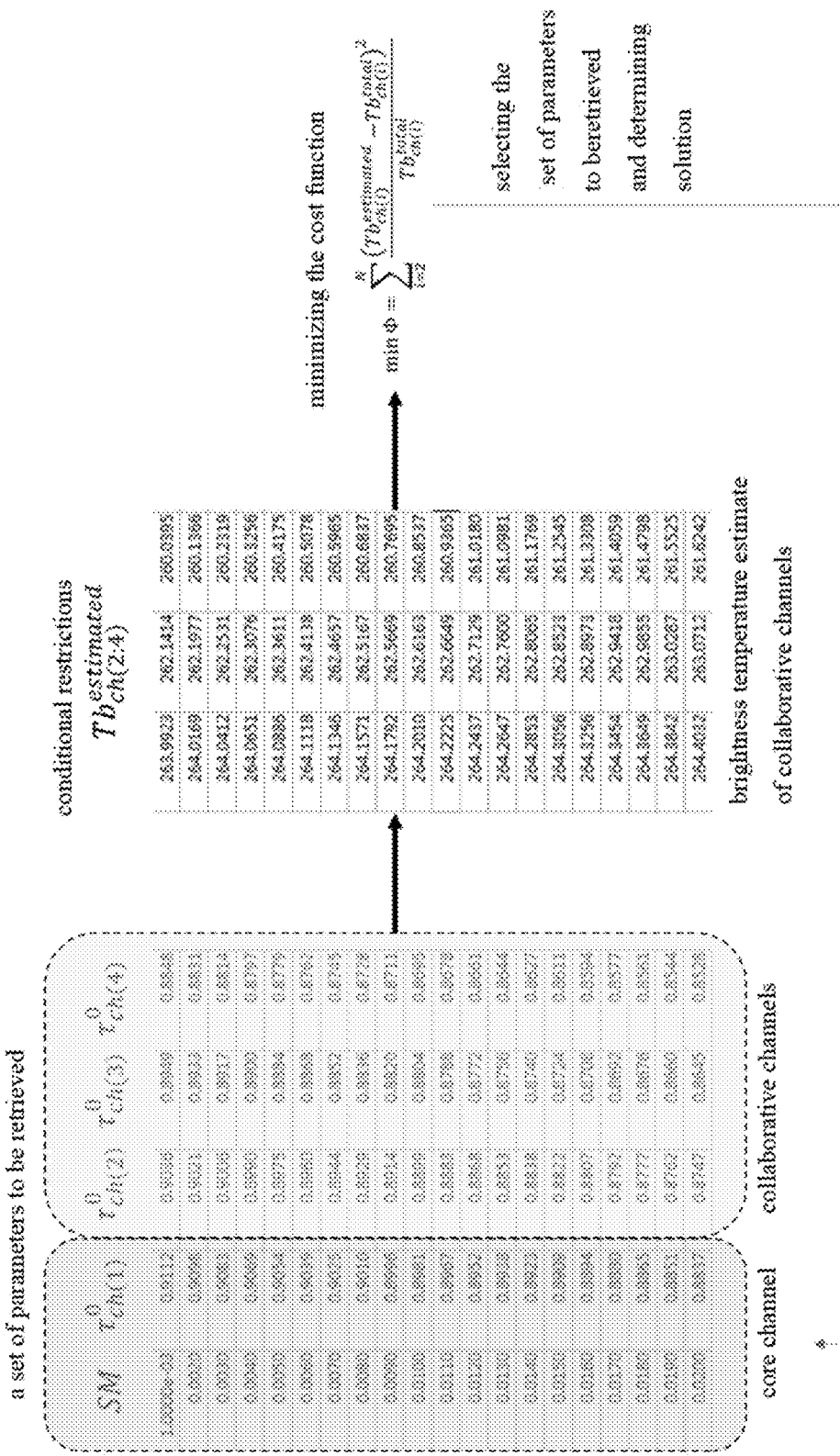
FIG. 2 is a schematic diagram according to the present invention.

The present invention will be described in further detail with reference to the accompanying drawings below in order to enable person skilled in the art to practice with reference to the description.

It should be noted that terms of "having", "containing" and "including/comprising" as used herein do not exclude presence or addition of one or more other elements or combinations thereof.

In a technical solution, as shown in FIG. 1, a method for soil moisture retrieval using multi-channel collaboration algorithm and passive microwave radiometry, including the following steps of:
establishing a mathematical relationship formula between brightness temperatures at any two channels according to a microwave radiative transfer equation;
collecting an actual brightness temperature of a core channel and actual brightness temperatures of collaborative channels;
selecting parameters to be retrieved, wherein the parameter comprises at least a soil moisture value;

giving a series of estimated values of the parameters to be retrieved, calculating a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value among the series of estimated values of the parameters to be retrieved according to a comparison result; or giving initial values of parameters to be retrieved, performing iterative calculation to obtain a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value according to the comparison result.

In the above technical solution, the microwave radiative transfer equation can be generally represented by a two-component model under the zero-order approximation (Omega-tau model) as follow:

$$Tb_{P,\theta,f}^{total} = f_v \cdot [e_{P,\theta,f}^v \cdot T_v + e_{P,\theta,f}^v \cdot (1-e_{P,\theta,f}^s) \cdot \Gamma_{P,\theta,f} \cdot T_v + e_{P,\theta,f}^s \cdot \Gamma_{P,\theta,f} \cdot T_s] + (1-f_v) \cdot e_{P,\theta,f}^s \cdot T_s \quad (1)$$

where the $Tb_{P,\theta,f}^{total}$ is total microwave radiation of soil surface observed at the polarization of P, incidence angle of $\theta$, and frequency of f. The values $T_v$ and $T_s$ are the physical temperatures of the vegetation and soil, respectively, $e_{P,\theta,f}^s$ is the microwave emissivity of the rough soil surface, and $e_{P,\theta,f}^v$ is the emissivity of the vegetation, which can be given by the equation $e_{P,\theta,f}^v = (1-\omega_{P,\theta,f})(1-\Gamma_{P,\theta,f})$, the $\omega_{P,\theta,f}$ is the effective single scattering albedo, and the $\Gamma_{P,\theta,f}$ is the vegetation transmissivity depending on the vegetation optical depth.

The mathematical relationship formula between brightness temperatures at any two channels is established according to the equation (1). The specific form of the mathematical relationship formula is not limited, as long as it can express the brightness temperature relationship at any two channels. At least one of frequency, incidence angle or polarization is different between the any two channels. The actual brightness temperature can be obtained by a microwave radiometer mounted on a platform such as satellites, airplanes, vehicles, and drones. The estimated value for soil moisture can be listed at fixed step intervals based on experience, preferably not greater than the soil moisture porosity. For an estimated value of any given parameter to be retrieved, predicted brightness temperatures of the collaborative channels are determined according to the actual brightness temperature of the core channel, equation (1) and the mathematical relationship formula. Alternatively giving initial values of parameters to be retrieved, an iterative algorithm is performed to obtain predicted brightness temperatures of the collaborative channels. The predicted brightness temperatures of the collaborative channels are compared with the actual brightness temperature. The collaborative channels with a minimum difference, namely a minimum value of the cost function, are selected and the estimated soil moisture value corresponding to the minimum value of the cost function from collaborative channels is taken as the soil moisture value. It can be seen that the retrieval process of the technical solution does not rely on the auxiliary data as inputs or constrains for vegetation properties, and it does not need to neglect the scattering effects and polarization dependences of vegetation. Multi-channel data are used to determine the parameters to be retrieved by the collaborative equation, which reduces the situation of multiple solutions and uncertainty during the retrieval process.

In other technical solutions, in some embodiments of the method for soil moisture retrieval using multi-channel collaboration algorithm and passive microwave radiometry, the microwave radiative transfer equation is represented by a two-component model under the zero-order approximation (Eq. 1) for convenient calculation.

In other technical solutions, in some embodiments of the method for soil moisture retrieval using multi-channel collaboration algorithm and passive microwave radiometry, the mathematical relationship formula is written as:

$$Tb_{ch(2)}^{total} = V_{ch(2)}^e - S_r V_r \cdot V_{ch(1)}^e + S_r V_r \cdot Tb_{ch(1)}^{total}$$

$$S_r = \frac{e_{ch(2)}^s}{e_{ch(1)}^s}$$

$$V_r = \frac{V_{ch(2)}^t}{V_{ch(1)}^t}$$

where $T_{ch(2)}^{total}$ and $Tb_{ch(1)}^{total}$ are brightness temperatures at any two channels, $e_{ch(2)}^s$ and $e_{ch(1)}^s$ are microwave emissivity of the rough soil surface at the any two channels, and $V_{ch(2)}^t$ and $V_{ch(1)}^t$ are vegetation emissions at the any two channels, and $V_{ch(1)}^s$ and $V_{ch(2)}^s$ are vegetation emission term of the any two channels.

In the technical solution, for better separation of soil and vegetation contribution, the two-component model under the zero-order approximation is rearranged as a two-component (soil and vegetation) form:

$$Tb_{ch}^{total} = V_{ch}^e + V_{ch}^t \cdot e_{ch}^s \quad (2)$$

$$V_{ch}^e = [f_v \cdot e_{ch}^v \cdot (1+\Gamma_{ch})] \cdot T_v \quad (3)$$

$$V_{ch}^t = [(1-f_v) + f_v \cdot \Gamma_{ch}] \cdot T_s - (f_v \cdot \Gamma_{ch} \cdot e_{ch}^v) \cdot T_v \quad (4)$$

where $V_{ch}^e$ is the vegetation emission term at the channel ch, and $V_{ch}^t$ is the vegetation transmission term.

For different channels, that is, when there are multiple channels to be observed, the soil emissivity of the different channels can be expressed as:

$$e_{ch(1)}^s = \frac{Tb_{ch(1)}^{total} - V_{ch(1)}^e}{V_{ch(1)}^t} \quad (5)$$

$$e_{ch(2)}^s = \frac{Tb_{ch(2)}^{total} - V_{ch(2)}^e}{V_{ch(2)}^t} \quad (6)$$

dividing Eq. (5) by Eq. (6), we obtain:

$$Tb_{ch(2)}^{total} = V_{ch(2)}^e - S_r V_r \cdot V_{ch(1)}^e + S_r V_r \cdot Tb_{ch(1)}^{total}, \quad (7)$$

wherein, $$S_r \frac{e_{ch(2)}^s}{e_{ch(1)}^s} \quad (8)$$

is the ratio of soil contribution, and $$V_r = \frac{V^t_{ch(2)}}{V^t_{ch(1)}} \qquad (9)$$

is the ratio of vegetation contribution in terms of transmission term.

The above equation clearly expresses the theoretical relationship between the brightness temperatures at any two channels (frequency, incidence angle or polarization) by the observation of the brightness temperature of the core channel ch(1) to predict the brightness temperature of the other collaborative channels ch(2), without any further assumptions. This relationship allows the consideration of vegetation effects differences in terms of frequency, incidence angle and polarization, and can be used to define and filter the parameters to be retrieved.

In other technical solutions, in some embodiments of the method for soil moisture retrieval using multi-channel collaboration algorithm and passive microwave radiometry, at least one of frequency, incidence angle or polarization is different between the any two channels of the core channel and the collaborative channels, such as the L-/C-/X-band, horizontal polarization and vertical polarization, or an incidence angle of 40-65 degrees.

In other technical solutions, in some embodiments of the method for soil moisture retrieval using multi-channel collaboration algorithm and passive microwave radiometry, according to estimated values of one or more parameters to be retrieved, the actual brightness temperature of the core channel, and the microwave radiative transfer equation, estimated values of other one or more parameters to be retrieved are calculated; values of the parameters to be retrieved of the collaborative channels are determined according to a relationship between parameters to be retrieved at any two channels; and the predicted brightness temperatures of the collaborative channels are calculated according to values of parameters to be retrieved of the collaborative channels and the mathematical relationship formula. In the technical solution, the microwave radiative transfer equation mainly includes the soil moisture, vegetation optical depth, the surface roughness parameter, the effective single scattering albedo, and other unknown parameters. One or more of the soil moisture, vegetation optical thickness, surface roughness parameter, and effective single scattering albedo can be used as parameters to be retrieved. Giving estimated values of one or more of the soil moisture and vegetation optical thickness, surface roughness parameter, and effective single scattering albedo, estimated values of one or more of parameters to be retrieved are calculated according to the microwave radiative transfer equation, and values of parameters to be retrieved of the collaborative channels are determined according to the relationship of the parameters to be retrieved. For example, the vegetation optical depths at different incidence angles and polarizations can be considered as equal, that is, the vegetation optical depth of the collaborative channels is the same as that of the core channel. On this basis, predicted brightness temperatures of the collaborative channels are calculated according to the mathematical relationship formula.

In other technical solutions, in some embodiments of the method for soil moisture retrieval using multi-channel collaboration algorithm and passive microwave radiometry, the number of channels comprised in the core channel and the collaborative channels is not less than the number of the parameters to be retrieved, which is convenient to solve the value of each parameter to be retrieved.

In other technical solutions, in some embodiments of the method for soil moisture retrieval using multi-channel collaboration algorithm and passive microwave radiometry, the parameters to be retrieved further comprise vegetation optical depth; and a relationship between vegetation optical depths at any two channels is:

$$\frac{\tau^0_{ch(1)}}{\tau^0_{ch(2)}} = \left(\frac{f_1}{f_2}\right)^x$$

where $\tau_{ch(1)}^0$ and $\tau_{ch(2)}^0$ are vegetation optical depths at frequency $f_1$ and frequency $f_2$, respectively, and x is a parameter depending on a vegetation type.

The influences from soil moisture and vegetation optical depth in the microwave radiative transfer equation are most significant, and the surface roughness parameters and effective single scattering albedo can be preset as needed. For a given surface roughness parameter (Rou) and the effective single scattering albedo ($\omega_{ch(2:N)}$), the microwave radiative transfer equation only comprises the unknown parameter $\{SM, \tau_{ch(1)}^0\}$. For example, the retrieval algorithm can be carried out in a traversal form as follows: for a set of parameters to be retrieved, giving the parameter of $\{Rou, \omega_{ch(1)}\}$, by assuming a series of soil moisture (SM) values (e.g. from 0.001 cm³/cm³ to its maximum porosity), a set of parameters $\tau_{ch(1)}^0$ could be obtained by resolving the vegetation optical depth by the microwave radiative transfer equation (1) with knowing the observed brightness temperature of the core channel $Tb_{ch(1)}^{total}$. A set of parameters $\tau_{ch(2:N)}^0$ can be obtained by assuming the relationship between vegetation optical depths of different channels, and the set of parameters to be retrieved is $\{SM, \tau_{ch(1)}^0\}$. Therefore, the soil moisture retrieved by this technical solution will have a good correspondent relationship with the retrieved vegetation optical depth, which reduces the occurrence of invalid solutions in the results.

Restricting conditions: a set of the brightness temperature $Tb_{ch(2:N)}^{estimated}$ observed at the collaborative channels can be calculated through Eq. (7) with the above obtained $\{SM, Rou, \omega_{ch(2:N)}, \tau_{ch(2:N)}^0\}$. It should be noted that they are estimated values obtained based on the Eq. (7) and assumed surface conditions.

In other technical solutions, in some embodiments of the method for soil moisture retrieval using multi-channel collaboration algorithm and passive microwave radiometry, the predicted brightness temperatures of the collaborative channels and the actual brightness temperature are compared by establishing a cost function. The specific form of the cost function is not limited in the technical solution, as long as it can express the difference between the predicted brightness temperatures and the actual brightness temperature.

In other technical solutions, in some embodiments of the method for soil moisture retrieval using multi-channel collaboration algorithm and passive microwave radiometry, the method comprises establishing the cost function, where the cost function is:

$$\min \Phi = \sum_{i=2}^{N} \frac{(Tb_{ch(i)}^{estimated} - Tb_{ch(i)}^{total})^2}{Tb_{ch(i)}^{total}};$$

selecting the minimum value of the cost function and an estimated soil moisture value corresponding to the minimum value of the cost function from comparison between predicted and actual observed brightness temperatures at the collaborative channels; and taking the estimated soil moisture value as the retrieval results of soil moisture value. The technical solution provides a preferred expression of the cost function, which is convenient for comparing the difference between the predicted brightness temperature of each collaborative channel and the actual brightness temperature, and is convenient for further determining the soil moisture value.

The present invention also provides a device for soil moisture retrieval using multi-channel collaboration algorithm and passive microwave radiometry base on the same inventive concept as the method for soil moisture retrieval using multi-channel collaboration algorithm and passive microwave radiometry, the device including:

a processor;

a memory, which stores executable instructions;

wherein, the processor is configured to execute the executable instruction for performing the method for soil moisture retrieval using multi-channel collaboration algorithm and passive microwave radiometry. This technical solution is based on the same inventive concept as the method for soil moisture retrieval using multi-channel collaboration algorithm and passive microwave radiometry. Please refer to the description in the method section. The device of the technical solution is not limited to PC, terminal, or server.

The present invention will be described in further detail with reference to two specific embodiments.

Figure 3A:
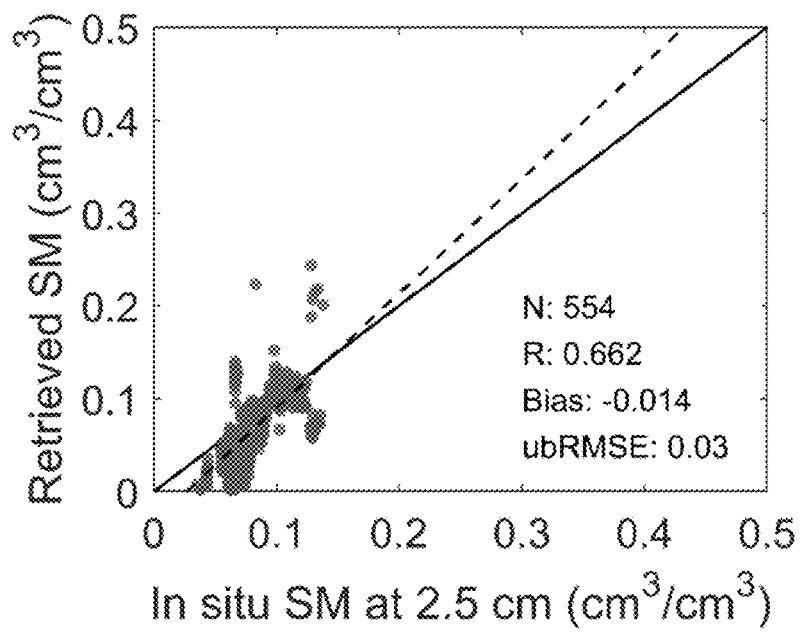
FIG. 3a is a retrieval result according to an embodiment of the present invention, Retrieved SM vs In situ SM.
Figure 3B:
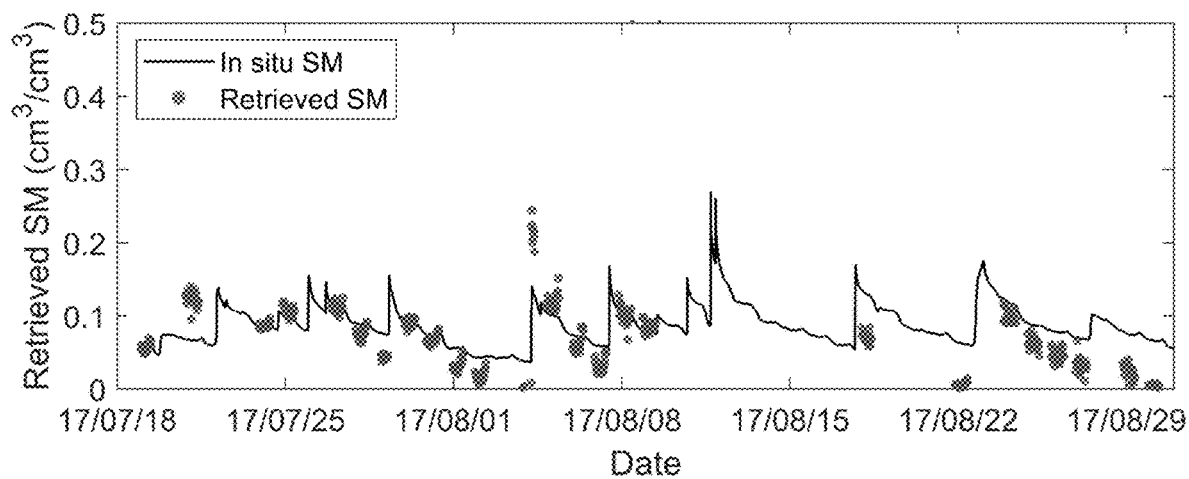
FIG. 3b is a retrieval result according to an embodiment of the present invention, Retrieved SM vs days.
Figure 3C:
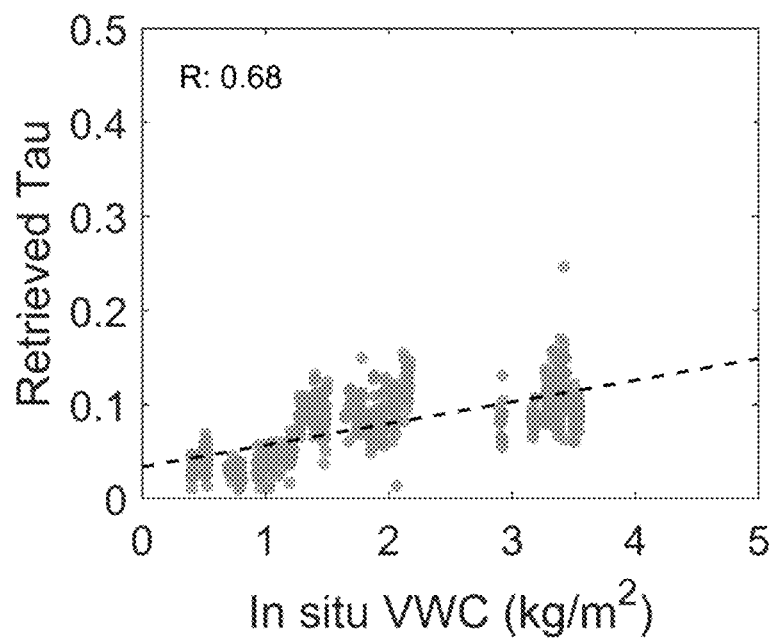
FIG. 3c is a retrieval result according to an embodiment of the present invention, Retrieved Tau vs In situ VWC.
Figure 3D:
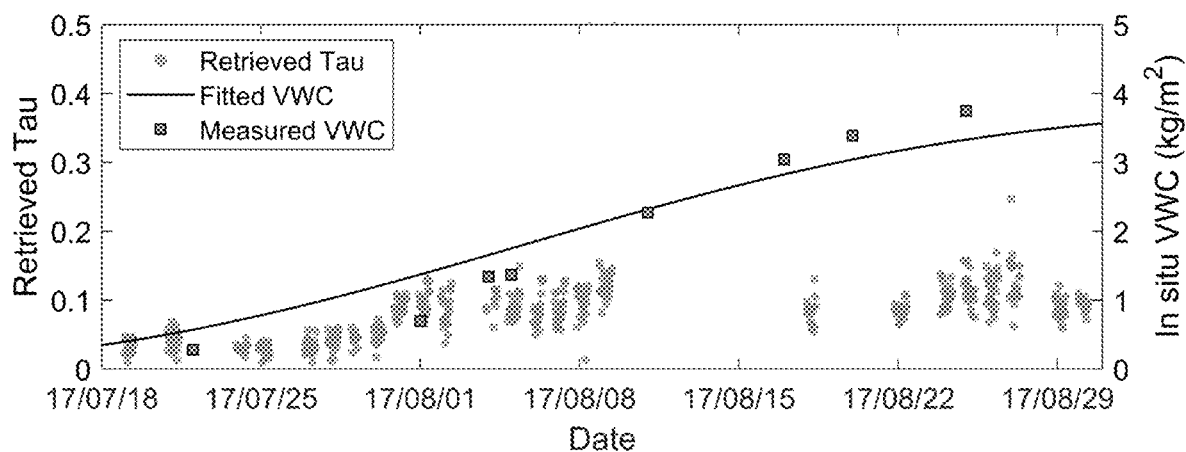
FIG. 3d is a retrieval result according to an embodiment of the present invention, Retrieved Tau vs days.

1. Retrieval results of the soil moisture and vegetation optical depth using the multi-channel collaborative algorithm based on the H polarization observation data of 40 to 65 degrees are shown in FIG. 3. The unbiased root-mean-square error (ubRMSE) with the actual measured value reaches 0.03 cm$^3$/cm$^3$. It can be seen that the retrieved vegetation optical depth has a good correlation with the actually measured vegetation moisture content, and there is no obvious correlation between the retrieved soil moisture and the vegetation optical depth. It shows that influences from the two are separated excellently, which is different from the unreasonable phenomenon of strong correlation between the two in the prior retrieval algorithm results.

Figure 4A:
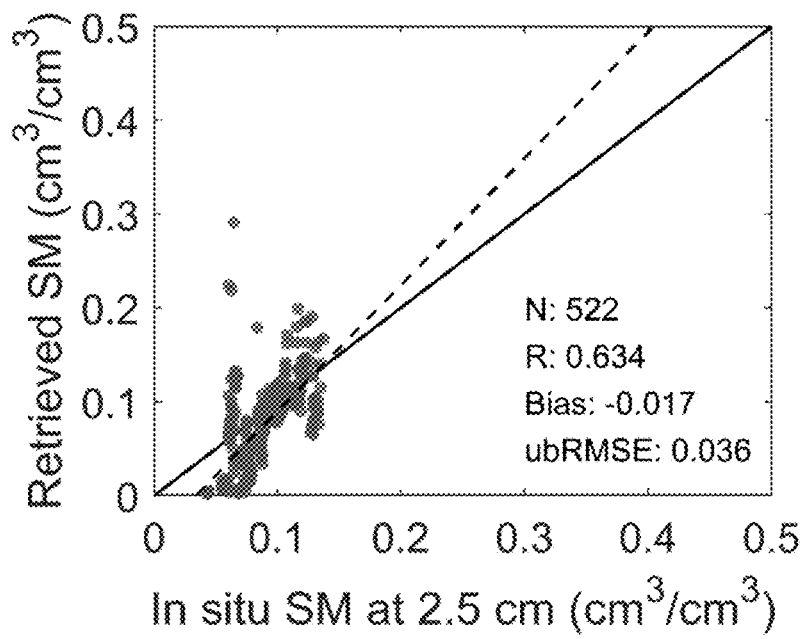
FIG. 4a is a retrieval result according to an embodiment of the present invention, Retrieved SM vs In situ SM.
Figure 4B:
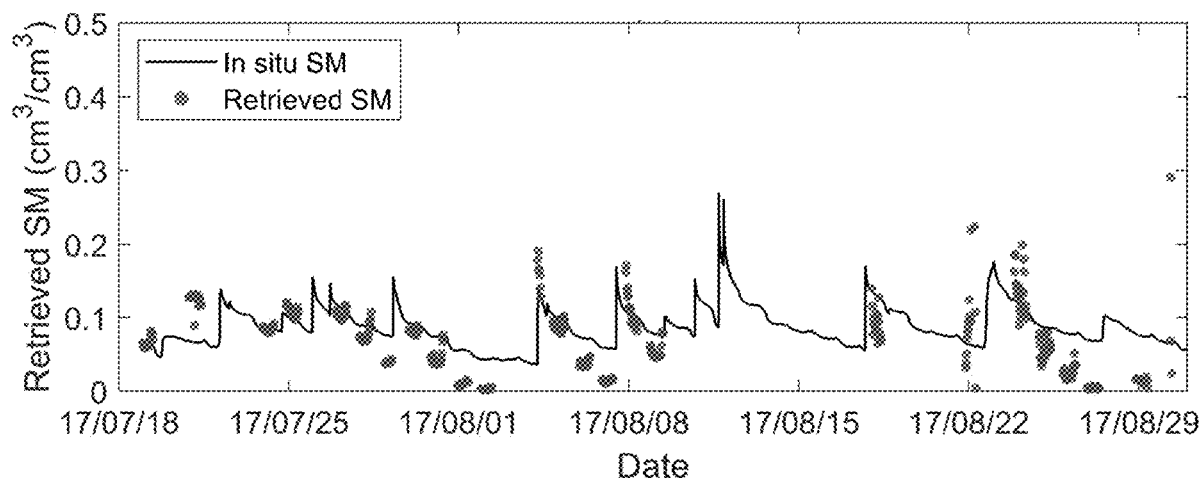
FIG. 4b is a retrieval result according to an embodiment of the present invention, Retrieved SM vs days.
Figure 4C:
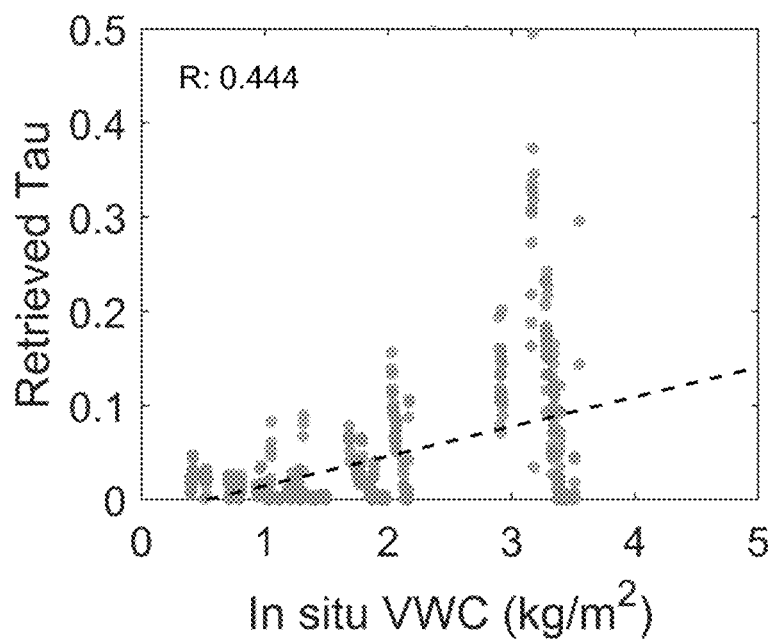
FIG. 4c is a retrieval result according to an embodiment of the present invention, Retrieved Tau vs In situ VWC.
Figure 4D:
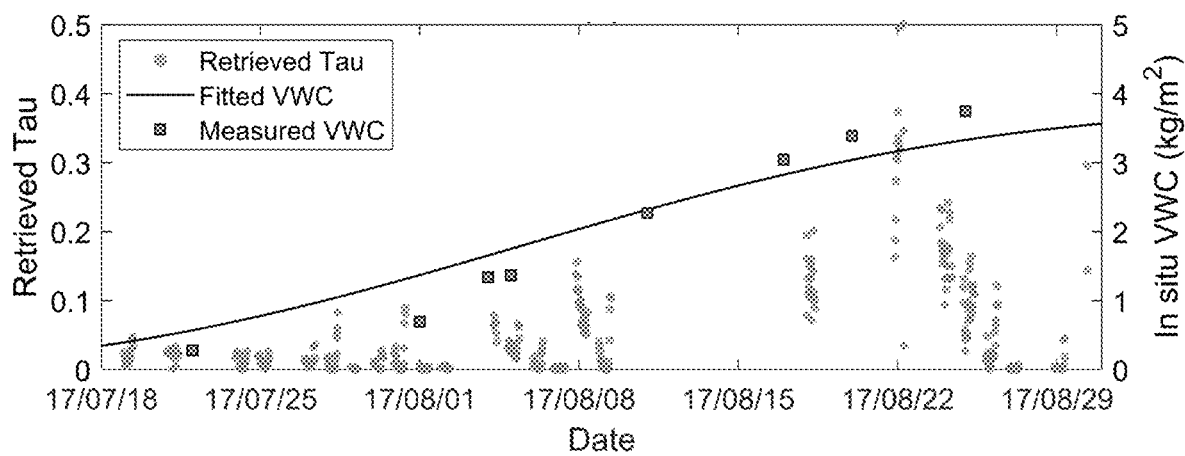
FIG. 4d is a retrieval result according to an embodiment of the present invention, Retrieved Tau vs days.

2. Retrieval results of the soil moisture and vegetation optical depth using the multi-channel collaborative algorithm based on the H polarization observation data at L-/C-/X bands are shown in FIG. 4. The unbiased root-mean-square error (ubRMSE) with the actually measured value reaches 0.036 cm$^3$/cm$^3$.

The number of devices and the treatment scale given herein are to simplify the description of the present invention. The application, modification and change of the method and device for soil moisture retrieval using multi-channel collaboration algorithm and passive microwave radiometry are apparent to those skilled in the field.

Although embodiments of the present invention have been disclosed as above, they are not limited to the applications listed in the specification and embodiments. They can be applied to all kinds of fields suitable for the present invention. Additional modifications can be easily implemented for those who are familiar with the field. Therefore, the present invention is not limited to specific details and the drawings shown and described herein without departing from the general concepts defined in the claims and the equivalents thereof.

What is claimed is:

1. A method for soil moisture retrieval using multi-channel collaboration algorithm and passive microwave radiometry, being characterized in that, the method comprises the following steps:

establishing a mathematical relationship formula between brightness temperatures at any two channels according to a microwave radiative transfer equation;

collecting an actual brightness temperature of a core channel and an actual brightness temperature of collaborative channels;

selecting parameters to be retrieved, wherein the parameters comprises at least a soil moisture value;

giving a series of estimated values of parameters to be retrieved, calculating a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value among the series of estimated values of parameters to be retrieved according to a comparison result;

or giving initial values of parameters to be retrieved, performing iterative calculation to obtain a series of predicted brightness temperatures of the collaborative channels according to the actual brightness temperature of the core channel, the microwave radiative transfer equation and the mathematical relationship formula, comparing the predicted brightness temperatures of the collaborative channels with the actual brightness temperature, and determining the soil moisture value according to the comparison result;

the microwave radiative transfer equation is represented by a two-component model under the zero-order approximation;

the mathematical relationship formula is written as:

$$Tb_{ch(2)}^{total} = V_{ch(2)}^{e} - S_r V_r \cdot V_{ch(1)}^{e} + S_r V_r \cdot Tb_{ch(1)}^{total}$$

$$S_r = \frac{e_{ch(2)}^s}{e_{ch(1)}^s}$$

$$V_r = \frac{V_{ch(2)}^t}{V_{ch(1)}^t}$$

wherein, $Tb_{ch(2)}^{total}$ and $Tb_{ch(1)}^{total}$ are brightness temperatures at any two channels, $e_{ch(2)}^s$ and $e_{ch(1)}^s$ are microwave emissivity of the rough soil surface at the any two channels, and $V_{ch(2)}^t$ and $V_{ch(1)}^t$ are vegetation emissions at the any two channels, and $V_{ch(2)}^e$ and $V_{ch(1)}^e$ are vegetation emission term of the any two channels.

2. The method for soil moisture retrieval using multi-channel collaboration algorithm and passive microwave radiometry according to claim 1, being characterized in that, at least one of frequency, incidence angle or polarization is different between the any two channels of the core channel and the collaborative channels.

3. The method for soil moisture retrieval using multi-channel collaboration algorithm and passive microwave radiometry according to claim 1, being characterized in that, according to estimated values of one or more parameters to be retrieved, the actual brightness temperature of the core channel, and the microwave radiative transfer equation, estimated values of other one or more parameters to be retrieved are calculated; the value of the parameters to be retrieved of the collaborative channels is determined according to a relationship between parameters to be retrieved at any two channels; and the predicted brightness temperatures of the collaborative channels are calculated according to the value of parameter to be retrieved of the collaborative channels and the mathematical relationship formula.

4. The method for soil moisture retrieval using multi-channel collaboration algorithm and passive microwave radiometry according to claim 3, being characterized in that, the number of channels comprised in the core channel and the collaborative channels is not less than the number of the parameters to be retrieved.

5. The method for soil moisture retrieval using multi-channel collaboration algorithm and passive microwave radiometry according to claim 3, being characterized in that, the parameter to be retrieved further comprises vegetation optical depth; and a relationship between vegetation optical depths at any two channels is:

$$\frac{\tau_{ch(1)}^0}{\tau_{ch(2)}^0} = \left(\frac{f_1}{f_2}\right)^x$$

wherein, $\tau_{ch(1)}^0$ and $\tau_{ch(2)}^0$ are vegetation optical depths at frequency $f_1$ and frequency $f_2$, respectively, and x is a parameter depending on a vegetation type.

6. The method for soil moisture retrieval using multi-channel collaboration algorithm and passive microwave radiometry according to claim 1, being characterized in that, the predicted brightness temperatures of the collaborative channels and the actual brightness temperature are compared by establishing a cost function.

7. The method for soil moisture retrieval using multi-channel collaboration algorithm and passive microwave radiometry according to claim 6, being characterized in that, the method comprises establishing the cost function, wherein the cost function is:

$$\min\Phi = \sum_{i=2}^{N} \frac{(Tb_{ch(i)}^{estimated} - Tb_{ch(i)}^{total})^2}{Tb_{ch(i)}^{total}};$$

selecting the minimum value of the cost function and an estimated soil moisture value corresponding to the minimum value of the cost function; and taking the estimated soil moisture value as the retrieval results of soil moisture value.

8. A retrieval device for soil moisture using passive microwave multichannel collaboration, comprising:

a processor;

a memory, which stores an executable instruction;

wherein, the processor is configured to execute the executable instruction for performing the method for soil moisture retrieval using multi-channel collaboration algorithm and passive microwave radiometry according to claim 1.

* * * * *